United States Patent
Shin et al.

(10) Patent No.: US 11,332,436 B2
(45) Date of Patent: May 17, 2022

(54) PROCESSES FOR PREPARING (E)-(2-(CHLOROMETHYL)-3-FLUOROALLYL) CARBAMATE COMPOUNDS

(71) Applicant: YUHAN CORPORATION, Seoul (KR)

(72) Inventors: Woo Seob Shin, Suwon-Si (KR); Cheol Hee Lim, Suwon-si (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 17/254,718

(22) PCT Filed: Jul. 1, 2019

(86) PCT No.: PCT/IB2019/055609
§ 371 (c)(1),
(2) Date: Dec. 21, 2020

(87) PCT Pub. No.: WO2020/008340
PCT Pub. Date: Jan. 9, 2020

(65) Prior Publication Data
US 2021/0230103 A1 Jul. 29, 2021

(30) Foreign Application Priority Data

Jul. 3, 2018 (KR) ........................ 10-2018-0076969

(51) Int. Cl.
C07C 271/14 (2006.01)
C07C 269/06 (2006.01)

(52) U.S. Cl.
CPC .......... *C07C 271/14* (2013.01); *C07C 269/06* (2013.01); *C07B 2200/13* (2013.01)

(58) Field of Classification Search
CPC . C07B 2200/13; C07C 269/06; C07C 271/14; C07C 269/08
See application file for complete search history.

(56) References Cited

U.S. PATENT DOCUMENTS

| 5,488,188 | A | 1/1996 | Evans et al. |
| 10,562,865 | B2 | 2/2020 | Han et al. |
| 10,899,719 | B2 | 1/2021 | Han et al. |
| 10,995,086 | B2 | 5/2021 | Han et al. |
| 11,091,479 | B2 | 8/2021 | Han et al. |
| 11,168,073 | B2 | 11/2021 | Han et al. |
| 2007/0293548 | A1 | 12/2007 | Wang et al. |
| 2020/0115352 | A1* | 4/2020 | Luo ................. C07D 261/20 |
| 2021/0147368 | A1 | 5/2021 | Han et al. |
| 2021/0317110 | A1 | 10/2021 | Han et al. |

FOREIGN PATENT DOCUMENTS

| WO | WO-2008/005670 A2 | 1/2008 |
| WO | WO-2009/066152 A2 | 5/2009 |
| WO | WO2013/163675 | * 11/2013 |
| WO | WO-2013/163675 A1 | 11/2013 |
| WO | WO2018/233633 | * 12/2018 |
| WO | WO-2019180644 | 9/2019 |
| WO | WO-2019180646 | 9/2019 |
| WO | WO-2020121261 | 6/2020 |
| WO | WO-2020121263 | 6/2020 |

OTHER PUBLICATIONS

International Search Report and Written Opinion on PCT/IB2019/055609 dated Oct. 16, 2019.

* cited by examiner

*Primary Examiner* — Brandon J Fetterolf
*Assistant Examiner* — Blaine G Doletski
(74) *Attorney, Agent, or Firm* — Sheppard Mullin Richter & Hampton LLP

(57) ABSTRACT

The present technology provides a process for selectively preparing an (E)-(2-(chloromethyl)-3-fluoroallyl)carbamate compound by refluxing an (E/Z)-(2-(chloromethyl)-3-fluoroallyl)carbamate compound in an organic solvent, followed by crystallization by cooling.

8 Claims, No Drawings

PROCESSES FOR PREPARING (E)-(2-(CHLOROMETHYL)-3-FLUOROALLYL) CARBAMATE COMPOUNDS

CROSS-REFERENCE TO RELATED APPLICATIONS

This application is the National Stage of International Patent Application No. PCT/IB2019/055609, filed Jul. 1, 2019, which claims the benefit of priority from Korean Patent Application No. 10-2018-0076969, filed on Jul. 3, 2018, the content of each of which is incorporated by reference herein in its entirety.

FIELD

The present technology relates to processes for preparing (E)-(2-(chloromethyl)-3-fluoroallyl)carbamate compounds. More specifically, the present technology relates to a process for selectively preparing (E)-(2-(chloromethyl)-3-fluoroallyl)carbamate compounds, comprising refluxing (E/Z)-(2-(chloromethyl)-3-fluoroallyl)carbamate compounds in an organic solvent, followed by crystallization by cooling.

BACKGROUND

The (E)- or (Z)-(2-(halomethyl)-3-fluoroallyl)carbamate compounds having N-protecting groups are useful as intermediates for preparing substituted 3-haloallylamine compounds that can be used in the preparation of vascular adhesion protein-1 (VAP-1) inhibitors. WO 2013/163675 discloses a process for preparing various 3-haloallylamine compounds from (E)- or (Z)-(2-(bromomethyl)-3-fluoroallyl)carbamate compounds having an N-protecting group via the substitution of a bromo group and the removal/substitution of an N-protecting group.

A process for preparing said intermediates disclosed in WO 2013/163675, i.e., (E)- or (Z)-(2-(bromomethyl)-3-fluoroallyl)carbamate compounds having an N-protecting group (a compound of Formula 1a' or a compound of Formula 1b'), is outlined in Reaction Scheme 1 below.

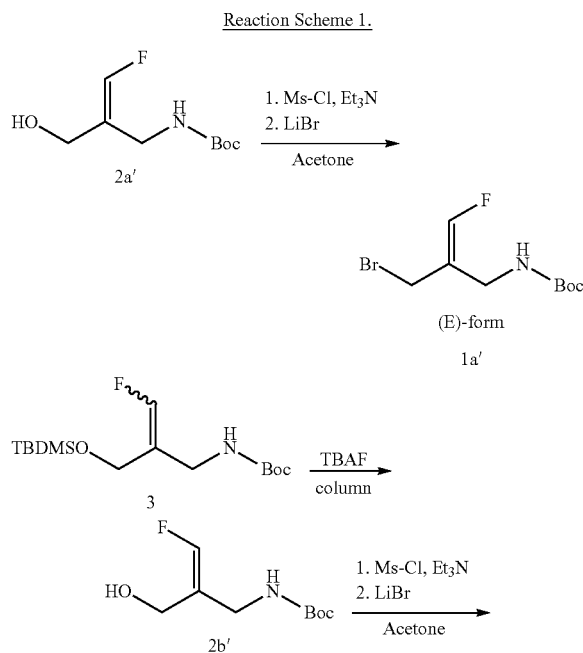

Reaction Scheme 1.

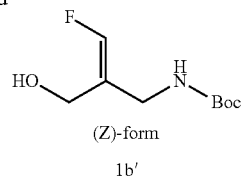

(Z)-form
1b'

Specifically, the process disclosed in WO 2013/163675 comprises the steps of reacting a compound of Formula 3 with tetrabutylammoniumfluoride (TBAF), followed by the separation of a reaction product using silica gel column chromatography to produce tert-butyl (E)-3-fluoro-(2-(hydroxymethyl)allylcarbamate (a compound of Formula 2a') and tert-butyl (Z)-3-fluoro-(2-(hydroxymethyl)allylcarbamate (a compound of Formula 2b'); and reacting said compound of Formula 2a' or said compound of Formula 2b' with methanesulfonyl chloride in the presence of triethylamine, followed by the reaction with lithium bromide to produce a corresponding tert-butyl (E)- or (Z)-(2-(bromomethyl)-3-fluoroallyl)carbamate.

The compound of Formula 2a' and the compound of Formula 2b' and the compounds obtained therefrom, i.e., a compound of Formula 1a' and a compound of Formula 1b', all are oil type compounds, and thus, cannot be separated according to a conventional crystallization process. Consequently, for the preparation of each of (E)- and (Z)- geometric isomers, i.e., a compound of Formula 2a' and a compound of Formula 2b', a separation process using silica gel column chromatography should be carried out as described in Reaction Scheme 1. Accordingly, it would be difficult to apply the preparation process disclosed in WO 2013/163675 for industrial scale, mass-production. Notably, the compound of Formula 2a' and compound of Formula 2b' obtained according to said preparation process exhibit yields of only 15.6% and 6.5%, respectively, and therefore, the target tert-butyl (E)- or (Z)-(2-(bromomethyl)-3-fluoroallyl) carbamate exhibits a low yield of 14.5% and 6.2%, respectively.

SUMMARY

The present inventors have conducted various studies in order to develop a process capable of selectively recrystallizing a specific geometric isomer of a (2-(halomethyl)-3-fluoroallyl)carbamate compound with a high yield, which is suitable for industrial scale, mass-production. As a result thereof, the present inventors discovered that if a compound of Formula 3 is converted to an (E/Z)-(2-(chloromethyl)-3-fluoroallyl)carbamate compound, wherein a chloro group is introduced as a halo group, the product thereof will be obtained as a solid, and if said (E/Z)-(2-(chloromethyl)-3-fluoroallyl)carbamate compound is refluxed in an organic solvent and then crystallized by cooling, an (E)-(2-(chloromethyl)-3-fluoroallyl)carbamate compound can be selectively prepared with a high yield. Further, said preparation process is advantageous in that it does not require a column chromatography process for the separation of geometric isomers.

Accordingly, it is an object of the present technology to provide a method of preparing and selectively isolating (E)-(2-(chloromethyl)-3-fluoroallyl)carbamate with a high yield that is suitable for industrial scale, mass-production.

According to one aspect of the present technology, there is provided a method of preparing a solid compound of Formula 1, the method comprising (a) refluxing a compound of Formula 1c in an organic solvent to form a reaction mixture and (b) crystallizing the reaction mixture by cooling to less than 20° C. to obtain the compound of Formula 1,

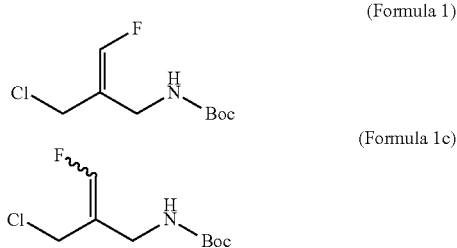

(Formula 1)

(Formula 1c)

wherein Boc is a nitrogen protecting group.

In some embodiments, said organic solvent is hexane, heptane, a mixed solvent of heptane and methyl ethyl ketone, a mixed solvent of heptane and toluene, a mixed solvent of heptane and methyl t-butyl ether, a mixed solvent of heptane and isopropyl alcohol, a mixed solvent of heptane and acetone, a mixed solvent of heptane and ethyl acetate, a mixed solvent of heptane and tetrahydrofuran, a mixed solvent of heptane and methyl isobutyl ketone, a mixed solvent of heptane and n-propanol, a mixed solvent of heptane and acetonitrile, a mixed solvent of heptane and isopropyl acetate, a mixed solvent of hexane and methyl ethyl ketone, a mixed solvent of hexane and toluene, a mixed solvent of hexane and methyl t-butyl ether, a mixed solvent of hexane and isopropyl alcohol, a mixed solvent of hexane and acetone, a mixed solvent of hexane and ethyl acetate, a mixed solvent of hexane and tetrahydrofuran, a mixed solvent of hexane and methyl isobutyl ketone, a mixed solvent of hexane and n-propanol, a mixed solvent of hexane and acetonitrile, or a mixed solvent of hexane and isopropyl acetate.

In some embodiments, said organic solvent is used in a proportion of 3 mL-7 mL with respect to 1 g of the compound of Formula 1c. In some embodiments, said refluxing is carried out at a temperature in the range of about 60° C. to about 80° C. In some embodiments, Step (b) is carried out via crystallization by cooling the reaction mixture to a temperature in a range of about −10° C. to about 20° C. In some embodiments, Step (b) is carried out via crystallization by cooling the reaction mixture for more than 1 hour.

In one embodiment, said compound of Formula 1c can be obtained by a method comprising (i) reacting a compound of Formula 3 with tetrabutylammonium fluoride to produce a compound of Formula 2; and (ii) reacting the compound of Formula 2 with methanesulfonyl chloride in the presence of a base, followed by the reaction with lithium chloride,

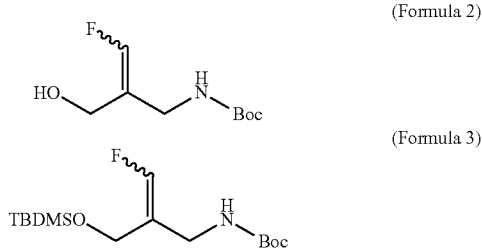

(Formula 2)

(Formula 3)

wherein Boc is a nitrogen protecting group and TBDMSO is tert-butyldimethylsilyloxy. In some embodiments, Step (ii) is carried out without isolating said compound of Formula 2 prepared in Step (i).

According to the present disclosure if an (E/Z)-(2-(chloromethyl)-3-fluoroallyl)carbamate compound, wherein a chloro group is introduced as a halo group, is refluxed in an organic solvent and then crystallized by cooling, an (E)-(2-(chloromethyl)-3-fluoroallyl)carbamate compound can be selectively prepared with a high yield. In one embodiment, the calculated yield by weight of the (E)-(2-(chloromethyl)-3-fluoroallyl)carbamate compound is at least about 60%. In another embodiment, the purity of the (E)-(2-(chloromethyl)-3-fluoroallyl)carbamate compound is demonstrated by $^1$H NMR and is at least about 99.5%.

That is, in the method according to the present technology, geometric isomers in the form of (E)- can be selectively prepared via stirring and refluxing/crystallization processes. Further, in the method according to the present technology, an (E)-(2-(chloromethyl)-3-fluoroallyl)carbamate compound used as an intermediate can be prepared in the form of a solid, which not only comes handy at the production site but is also convenient in that a column chromatography separation process can be avoided. Thus, the method according to the present technology is suitable for industrial-scale, mass production. Further, the method according to the present technology is capable of shortening the manufacture process by omitting the separation process of a compound of Formula 2, which corresponds to a compound of Formula 2a' and a compound of Formula 2b'.

According to another aspect of the present technology, there is provided a compound of Formula 1,

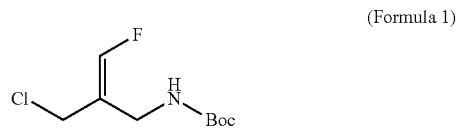 [SMILES: CC(C)(C)OC(=O)NC/C(=C\F)CCl]

(Formula 1)

wherein Boc is a nitrogen protecting group and the compound is a solid.

DETAILED DESCRIPTION

The present technology provides a method of preparing a solid compound of Formula 1, the method comprising (a) refluxing a compound of Formula 1c in an organic solvent to form a reaction mixture and (b) crystallizing the reaction mixture by cooling, to less than 20° C. to obtain the compound of Formula 1,

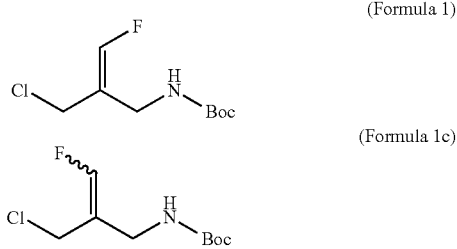

(Formula 1)

(Formula 1c)

wherein Boc is a nitrogen protecting group. Said nitrogen protecting group may be, for example, t-butoxy, benzyl, acetyl, benzoyl, or carbobenzoyl.

It was found by the present technology that if an (E/Z)-(2-(chloromethyl)-3-fluoroallyl)carbamate compound is refluxed in an organic solvent and then crystallized by cooling, an (E)-(2-(chloromethyl)-3-fluoroallyl)carbamate compound can be selectively prepared with a high yield. In one embodiment, the calculated yield by weight of the (E)-(2-(chloromethyl)-3-fluoroallyl)carbamate compound is at least about 60%. In another embodiment, the purity of the (E)-(2-(chloromethyl)-3-fluoroallyl)carbamate compound is demonstrated by $^1$H NMR and is at least about 99.5%.

In particular, it was discovered that if a compound of Formula 1c wherein an (E)-geometric isomer and a (Z)-geometric isomer are mixed, is subjected to refluxing and then to crystallization by cooling, an (E)-geometric isomer, i.e., an (E)-(2-(chloromethyl)-3-fluoroallyl)carbamate compound, is selectively obtained as a solid. That is, the method according to the present technology provides an (E)-(2-(chloromethyl)-3-fluoroallyl)carbamate compound as a solid, wherein an E/Z form ratio is in the range of 99.50:0.50 to 99.95:0.05 according to $^1$H NMR analysis.

For the methods of the present technology, the organic solvent unlimitedly comprises a solvent or a mixed solvent that is capable of dissolving a compound of Formula 1c. Said organic solvent may be in the form of a single solvent or a mixed solvent. If said organic solvent is in the form of a single organic solvent, an organic solvent such as hexane or heptane can be used. Further, if the organic solvent is in the form of a mixed solvent, an organic solvent such as a mixed solvent of an organic solvent that is miscible with heptane and heptane or a mixed solvent of an organic solvent that is miscible with hexane and hexane can be used. The exemplary mixed solvents may include a mixed solvent of heptane and methyl ethyl ketone, a mixed solvent of heptane and toluene, a mixed solvent of heptane and methyl t-butyl ether, a mixed solvent of heptane and isopropyl alcohol, a mixed solvent of heptane and acetone, a mixed solvent of heptane and ethyl acetate, a mixed solvent of heptane and tetrahydrofuran, a mixed solvent of heptane and methyl isobutyl ketone, a mixed solvent of heptane and n-propanol, a mixed solvent of heptane and acetonitrile, a mixed solvent of heptane and isopropyl acetate, a mixed solvent of hexane and methyl ethyl ketone, a mixed solvent of hexane and toluene, a mixed solvent of hexane and methyl t-butyl ether, a mixed solvent of hexane and isopropyl alcohol, a mixed solvent of hexane and acetone, a mixed solvent of hexane and ethyl acetate, a mixed solvent of hexane and tetrahydrofuran, a mixed solvent of hexane and methyl isobutyl ketone, a mixed solvent of hexane and n-propanol, a mixed solvent of hexane and acetonitrile, and a mixed solvent of hexane and isopropyl acetate.

If a mixed solvent is used as said organic solvent, e.g., in the case where said heptane or hexane is used together with another organic solvent other than said heptane or hexane, the ratio of heptane or hexane with another organic solvent may be, for example, a volume ratio of 90:10 to 100:0.5, and preferably a volume ratio of about 50:3.

For the methods according to the present technology, the organic solvent can be used in a proportion of 3 mL-7 mL with respect to 1 g of a compound of Formula 1c. Further, said stirring and refluxing can be carried out within the range of the reflux temperature of the organic solvent as used, for example, at a temperature in the range of 40° C.-118° C., and preferably, in the range of 60° C.-80° C.

For the methods according to the present technology, the cooling temperature is not specifically limited as long as it is sufficient to cause crystallization. For example, Step (b) can be carried out via crystallization by cooling the reaction mixture of Step (a) to a temperature in the range of about −10° C. to about 20° C. If said temperature is below −10° C., an E/Z isomer can be mixed. If the temperature exceeds 20° C., it may result in a low yield. In some embodiments, Step (b) is carried out via crystallization by cooling the reaction mixture for more than 1 hour.

For the methods according to the present technology, the compound of Formula 1c can be obtained by a method comprising (i) reacting a compound of Formula 3 with tetrabutylammoniumfluoride to produce a compound of Formula 2; and (ii) reacting the compound of Formula 2 with methanesulfonyl chloride in the presence of a base, followed by the reaction with lithium chloride,

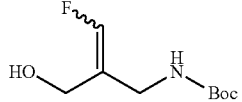

(Formula 2)

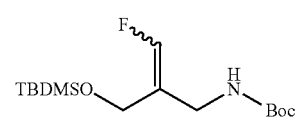

(Formula 3)

wherein Boc is a nitrogen protecting group and TBDMSO is tert-butyldimethylsilyloxy. Said nitrogen protecting group may be, for example, t-butoxy, benzyl, acetyl, benzoyl, or carbobenzoyl.

Said reaction of Step (i) can be carried out in the same manner as that disclosed in WO 2013/163675. Further, in Step (ii), the reaction of a compound of Formula 2 with methanesulfonyl chloride in the presence of a base (e.g., triethylamine, etc.) can be carried out in the same manner as that disclosed in WO 2013/163675.

The reaction product of said compound of Formula 2 and methanesulfonyl chloride can be subjected to the reaction with lithium chloride for about 1-5 hours in an organic solvent such as acetone, dichloromethane, methylethylketone, ethylacetate, etc. Said lithium chloride may be used in a proportion of 1.0 to 3.0 equivalents relative to 1 equivalent of the reaction product of the compound of Formula 2 and methanesulfonyl chloride, but is not limited thereto. The product obtained from said reaction, i.e., a compound of Formula 1c, can be isolated by known methods such as conventional extraction, concentration, etc.

The present technology also found that the separation (isolation) process of a compound of Formula 2 can be omitted in the reaction of Step (i) and Step (ii). Thus, in one embodiment, the preparation process can be further shortened by carrying out the reaction in Step (ii) without isolating the compound of Formula (2) prepared in Step (i).

A reaction scheme for the preparation of a compound of Formula 1 from a compound of Formula 3, is illustrated in Reaction Scheme 2 below.

Reaction Scheme 2.

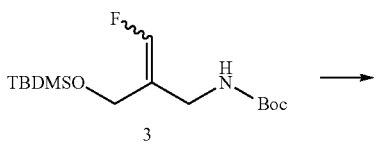

3

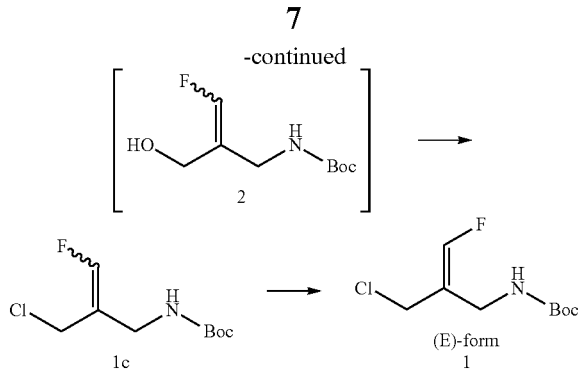

In Reaction Scheme 2, Boc is a nitrogen protecting group and TBDMSO is tert-butyldimethylsilyloxy. Said nitrogen protecting group may be, for example, t-butoxy, benzyl, acetyl, benzoyl, or carbobenzoyl.

Accordingly, the present technology also provides a compound of Formula 1, (Formula 1)

wherein Boc is a nitrogen protecting group and the compound is a solid.

Hereinafter, the present technology is further elaborated through examples. However, the following examples are provided for illustration purposes only, and are not intended to limit the scope of the invention.

EXAMPLES

Example 1. tert-butyl (E)-(2-(chloromethyl)-3-fluoroallyl)carbamate (1) Step 1: tert-butyl (2-(chloromethyl)-3-fluoroallyl)carbamate

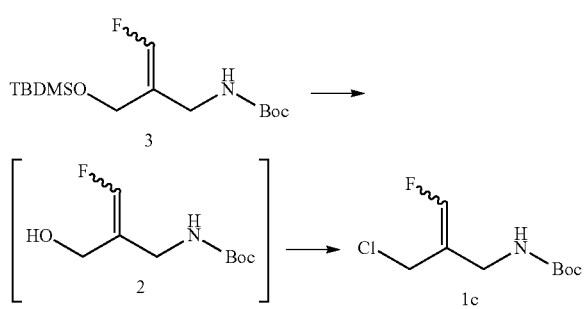

Tert-butyl (2-(((tert-butyldimethylsilyl)oxy)methyl)-3-fluoroallyl)carbamate (155.6 g, 0.487 mol) was added to tetrahydrofuran (778 mL) and then tetrabutylammonium fluoride (1.0 M in THF; 58.4 mL, 0.584 mol) was added thereto at room temperature. The reaction mixture was stirred for 1 hour and then water (1,500 mL) and ethyl acetate (1,000 mL) was added to extract an organic layer. To the residue obtained from the concentration of the organic layer, acetone (1000 mL) was added. The resultant mixture thereof was cooled to about 10° C., followed by the dropwise addition of triethylamine (98.6 g, 0.974 mol) and methanesulfonyl chloride (69.8 g, 0.609 mol). The resulting solution was stirred at the same temperature for 1 hour and filtered to separate the hydrochloride produced during the reaction. The separated hydrochloride was washed with acetone (1,000 mL), and the resulting wash liquid was combined with the filtrate and then concentrated until about 1,000 mL of acetone was obtained. Lithium chloride (41.31 g, 0.974 mol) was added to the concentrated solution. The resulting solution was stirred at room temperature for 1 hour. Purified water (1,000 mL) and ethyl acetate (1,000 mL) was added to the reaction mixture, followed by layer separation. The organic layer thus obtained was concentrated under reduced pressure to give a title compound. The obtained title compound was used in the subsequent reaction.

(2) Step 2: tert-butyl (E)-(2-(chloromethyl)-3-fluoroallyl)carbamate

Heptane (500 mL) was introduced to tert-butyl (2-(chloromethyl)-3-fluoroallyl)carbamate prepared in Step 1. The resulting mixture was subjected to stirring and refluxing, then slowly cooled over the course of at least one hour to 0° C., and stirred for 1 hour. The reaction mixture was filtered to obtain a solid which was then dried at about 30° C. to give 67.8 g of the title compound.

The total yield of the product, i.e., the production yield from a compound of Formula 3 to a compound of Formula 1, is 62.3%. The $^1$H NMR (Bruker 400 MHz instrument) analysis result of the obtained product is as follows: $^1$H NMR (400 MHz, CDCl$_3$) δ ppm: 1.45(9H, s), 3.99(2H, s), 4.05(2H, s), 4.74 (1H, s), 6.73 (1H, d, J=81.2 Hz).

Further, Table 1 below shows the analysis results where the product of Steps 1 and 2 was analyzed by $^1$H NMR and then the E/Z form ratio was calculated. The E/Z form ratio was calculated by using characteristic $^1$H NMR peaks for the E isomer (~6.8 ppm) and the Z isomer (~6.7 ppm). More particularly, the E/Z form ratio is calculated from the integration of these two peaks, normalized so that sum of the integration is equal to 100.

TABLE 1

| Product | | E-form | Z-form |
|---|---|---|---|
| Step 1 | tert-butyl (2-(chloromethyl)-3-fluoroallyl) carbamate | 72.3 | 27.3 |
| Step 2 | tert-butyl (E)-(2-(chloromethyl)-3-fluoroallyl) carbamate | 99.52 | 0.48 |

Examples 2-13

Tert-butyl (E)-(2-(chloromethyl)-3-fluoroallyl)carbamate was prepared in the same fashion as Example 1 except that the solvent or mixed solvent described in Table 2 was used instead of heptane.

The results from the ¹H NMR analysis (conducted as described in Example 1) of the products obtained from Examples 2-13 were comparable to that of Example 1. The total yield of the products obtained from Examples 2-13 (i.e., the production yield from a compound of Formula 3 to a compound of Formula 1) and the E/Z-form ratio obtained from the NMR analysis are shown in Table 2.

TABLE 2

| Example | Solvent | Total yield | E-form | Z-form |
|---|---|---|---|---|
| 2 | hexane (500 mL) | 61.2% | 99.51 | 0.49 |
| 3 | a mixed solvent of heptane (500 mL) and methyl ethyl ketone (30 mL) | 67.8% | 99.98 | 0.02 |
| 4 | a mixed solvent of heptane (500 mL) and toluene (30 mL) | 60.8% | 99.94 | 0.06 |
| 5 | a mixed solvent of heptane (500 mL) and methyl tert-butyl ether (30 mL) | 63.4% | 99.93 | 0.07 |
| 6 | a mixed solvent of heptane (500 mL) and isopropyl alcohol (30 mL) | 64.1% | 99.91 | 0.09 |
| 7 | a mixed solvent of heptane (500 mL) and acetone(30 mL) | 61.3% | 99.94 | 0.06 |
| 8 | a mixed solvent of heptane (500 mL) and ethyl acetate (30 mL) | 63.8% | 99.95 | 0.05 |
| 9 | a mixed solvent of heptane (500 mL) and tetrahydrofuran (30 mL) | 62.9% | 99.89 | 0.11 |
| 10 | a mixed solvent of heptane (500 mL) and methyl isobutyl ketone (30 mL) | 63.5% | 99.96 | 0.04 |
| 11 | a mixed solvent of heptane (500 mL) and n-propanol (30 mL) | 61.7% | 99.95 | 0.05 |
| 12 | a mixed solvent of heptane (500 mL) and acetonitrile (30 mL) | 60.1% | 99.85 | 0.15 |
| 13 | a mixed solvent of heptane (500 mL) and isopropyl acetate (30 mL) | 63.7% | 99.92 | 0.08 |

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The invention claimed is:

1. A method of preparing a solid compound of Formula 1, the method comprising (a) refluxing a compound of Formula 1c in an organic solvent to form a reaction mixture; and (b) cooling the reaction mixture to less than or about 20° C. to obtain the solid compound of Formula 1,

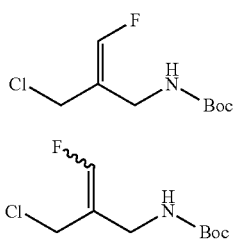

(Formula 1)

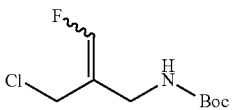

(Formula 1c)

wherein Boc is a nitrogen protecting group.

2. The method of claim 1, wherein said organic solvent is hexane, heptane, a mixed solvent of heptane and methyl ethyl ketone, a mixed solvent of heptane and toluene, a mixed solvent of heptane and methyl t-butyl ether, a mixed solvent of heptane and isopropyl alcohol, a mixed solvent of heptane and acetone, a mixed solvent of heptane and ethyl acetate, a mixed solvent of heptane and tetrahydrofuran, a mixed solvent of heptane and methyl isobutyl ketone, a mixed solvent of heptane and n-propanol, a mixed solvent of heptane and acetonitrile, a mixed solvent of heptane and isopropyl acetate, a mixed solvent of hexane and methyl ethyl ketone, a mixed solvent of hexane and toluene, a mixed solvent of hexane and methyl t-butyl ether, a mixed solvent of hexane and isopropyl alcohol, a mixed solvent of hexane and acetone, a mixed solvent of hexane and ethyl acetate, a mixed solvent of hexane and tetrahydrofuran, a mixed solvent of hexane and methyl isobutyl ketone, a mixed solvent of hexane and n-propanol, a mixed solvent of hexane and acetonitrile, or a mixed solvent of hexane and isopropyl acetate.

3. The method of claim 1, wherein said organic solvent is used in a proportion of 3 mL-7 mL with respect to 1 g of the compound of Formula 1c.

4. The method of claim 1, wherein said refluxing is carried out at a temperature of about 60° C. to about 80° C.

5. The method of claim 1, wherein cooling the reaction mixture is at a temperature of about −10° C. to about 20° C.

6. The method of claim 1, wherein cooling the reaction mixture is for more than 1 hour.

7. The method of claim 1, wherein said compound of Formula 1c is obtained by a method comprising (i) reacting a compound of Formula 3 with tetrabutylammonium fluoride to provide a compound of Formula 2; and (ii) reacting said compound of Formula 2 with methanesulfonyl chloride in the presence of a base, followed by reaction with lithium chloride,

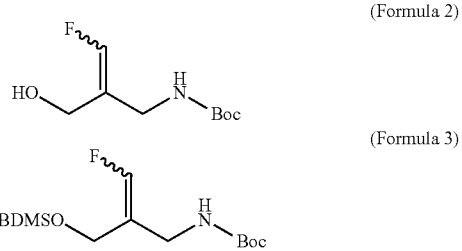

(Formula 2)

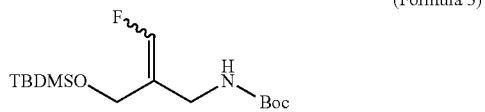

(Formula 3)

wherein Boc is a nitrogen protecting group and TBDMSO is tert-butyldimethylsilyloxy.

8. The method of claim 7, wherein Step (ii) is carried out without isolating said compound of Formula 2 prepared in Step (i).

* * * * *